(12) United States Patent
Deppermann

(10) Patent No.: US 7,600,642 B2
(45) Date of Patent: Oct. 13, 2009

(54) HIGH THROUGHPUT AUTOMATED SEED ANALYSIS SYSTEM

(75) Inventor: Kevin L. Deppermann, St. Charles, MO (US)

(73) Assignee: Monsanto Technology, LLC, St. Louis, MO (US)

( * ) Notice: Subject to any disclaimer, the term of this patent is extended or adjusted under 35 U.S.C. 154(b) by 0 days.

(21) Appl. No.: 10/945,811

(22) Filed: Sep. 21, 2004

(65) Prior Publication Data

US 2005/0082207 A1  Apr. 21, 2005

(51) Int. Cl.
- B07C 5/00 (2006.01)
- A01G 23/10 (2006.01)
- A01G 29/00 (2006.01)
- A01C 1/00 (2006.01)

(52) U.S. Cl. .................... 209/552; 209/576; 47/14; 47/58.1 LS; 47/58.1 SE

(58) Field of Classification Search ............... 209/552, 209/557, 576, 586, 905, 919, 936, 939, 510, 209/511; 198/402, 403, 406, 377.1, 378, 198/404; 356/928, 929, 941; 47/1.01 P, 47/14, 58.1 SE, 58.1 LS; 422/63–65
See application file for complete search history.

(56) References Cited

U.S. PATENT DOCUMENTS

| | | | |
|---|---|---|---|
| 2,756,903 A | 7/1956 | Kreidler | |
| 3,530,372 A * | 9/1970 | Laukien | ........................ 324/318 |
| 3,642,128 A | 2/1972 | Westwood et al. | |
| 3,852,914 A | 12/1974 | Levengood | |
| 3,861,788 A | 1/1975 | Webster | |
| 4,037,970 A | 7/1977 | Webster et al. | |
| 4,040,747 A | 8/1977 | Webster | |
| 4,260,262 A | 4/1981 | Webster | |

(Continued)

FOREIGN PATENT DOCUMENTS

DE     198 45 883     5/1999

(Continued)

OTHER PUBLICATIONS

"Rapid identification of organic contaminants in pretreated waste water using AOTF near-IR spectrometry", ISA 1995 Meeting Proceedings, pp. 87-95 (1995).

(Continued)

Primary Examiner—Patrick H Mackey
Assistant Examiner—Mark Hageman
(74) Attorney, Agent, or Firm—James E. Davis; Joseph A. Schaper; Harness, Dickey & Pierce, P.L.C.

(57) ABSTRACT

A transport subsystem conveys seed holding well trays between a plurality of stations. A loading subsystem is positioned at a first station and is operable to load seeds into individual wells of the conveyed tray. An imaging subsystem is positioned at a second station and is operable to image the seeds contained within the tray wells. A mechanism is provided for flipping the seeds so as to enable the imaging subsystem to obtain multi-side seed images. A sorting subsystem is positioned at a third station and is operable to remove the seeds from the tray wells and sort the removed seeds into a plurality of sort bins. The sorting determination may be made based on an analysis of the seed images obtained by the imaging subsystem.

34 Claims, 9 Drawing Sheets

U.S. PATENT DOCUMENTS

| | | | |
|---|---|---|---|
| 4,375,854 A | 3/1983 | Hedel | |
| 4,480,765 A | 11/1984 | Tonus | |
| 4,654,592 A | 3/1987 | Zens | |
| 4,734,584 A | 3/1988 | Rosenthal | |
| 4,752,689 A | 6/1988 | Satake | |
| 4,818,380 A * | 4/1989 | Azegami et al. | 209/565 |
| 4,884,696 A * | 12/1989 | Peleg | 209/545 |
| 4,931,061 A | 6/1990 | Young | |
| 4,946,046 A * | 8/1990 | Affleck et al. | 209/580 |
| 5,051,699 A | 9/1991 | Hanawa | |
| 5,132,538 A | 7/1992 | Norris | |
| 5,221,518 A | 6/1993 | Mills | |
| 5,245,188 A * | 9/1993 | Satake et al. | 250/341.7 |
| 5,253,302 A | 10/1993 | Massen | |
| 5,412,220 A * | 5/1995 | Moore | 250/559.48 |
| 5,475,221 A | 12/1995 | Wang | |
| 5,533,145 A | 7/1996 | Shofner et al. | |
| 5,590,791 A * | 1/1997 | Gschweitl | 209/577 |
| 5,668,374 A | 9/1997 | DiFoggio et al. | |
| 5,669,511 A * | 9/1997 | Satake et al. | 209/580 |
| 5,733,592 A * | 3/1998 | Wettstein et al. | 426/416 |
| 5,751,421 A | 5/1998 | Wright et al. | |
| 5,764,819 A | 6/1998 | Orr et al. | |
| 5,833,947 A | 11/1998 | Rocklage | |
| 5,836,438 A * | 11/1998 | Jung | 198/402 |
| 5,837,458 A | 11/1998 | Minshull et al. | |
| 5,864,984 A * | 2/1999 | McNertney | 47/58.1 R |
| 5,918,977 A | 7/1999 | Borggaard et al. | |
| 5,991,025 A | 11/1999 | Wright et al. | |
| 6,096,944 A | 8/2000 | Vierling et al. | |
| 6,100,526 A | 8/2000 | Mayes | |
| 6,150,158 A * | 11/2000 | Bhide et al. | 435/286.3 |
| 6,237,286 B1 | 5/2001 | Williams | |
| 6,266,864 B1 | 7/2001 | Barber | |
| 6,537,826 B1 | 3/2003 | Horigane | |
| 6,646,264 B1 * | 11/2003 | Modiano et al. | 250/339.07 |
| 6,705,827 B2 | 3/2004 | Keller et al. | |
| 6,706,989 B2 | 3/2004 | Hunter et al. | |
| 6,782,991 B2 * | 8/2004 | Johansson | 198/401 |
| 6,809,819 B1 | 10/2004 | Vinjamoori et al. | |
| 6,879,389 B2 * | 4/2005 | Meyer et al. | 356/237.1 |
| 7,044,306 B2 | 5/2006 | Deppermann | |
| 7,367,155 B2 | 5/2008 | Kotyk et al. | |
| 2001/0013486 A1 * | 8/2001 | Yamakawa | 209/574 |
| 2001/0014750 A1 | 8/2001 | Ulrich et al. | |
| 2002/0144458 A1 | 10/2002 | Hunter et al. | |
| 2003/0142852 A1 | 7/2003 | Lu et al. | |
| 2004/0072143 A1 | 4/2004 | Timmis | |
| 2004/0141641 A1 * | 7/2004 | McDonald et al. | 382/159 |
| 2004/0160607 A1 | 8/2004 | Lin et al. | |
| 2004/0221335 A1 | 11/2004 | Shewmaker et al. | |
| 2005/0082207 A1 | 4/2005 | Deppermann | |
| 2006/0006335 A1 | 1/2006 | Lawrence et al. | |
| 2006/0042527 A1 | 3/2006 | Deppermann | |
| 2006/0042528 A1 | 3/2006 | Deppermann | |
| 2006/0046244 A1 | 3/2006 | Deppermann | |
| 2006/0046264 A1 | 3/2006 | Deppermann et al. | |
| 2006/0048247 A1 | 3/2006 | Deppermann | |
| 2006/0048248 A1 | 3/2006 | Deppermann | |
| 2006/0112628 A1 * | 6/2006 | Kotyk et al. | 47/58.1 SE |
| 2007/0204366 A1 | 8/2007 | Deppermann et al. | |
| 2007/0207485 A1 | 9/2007 | Deppermann et al. | |
| 2008/0113367 A1 | 5/2008 | Becker et al. | |
| 2008/0131254 A1 | 6/2008 | Cope et al. | |
| 2008/0131924 A1 | 6/2008 | Cope et al. | |

FOREIGN PATENT DOCUMENTS

| | | |
|---|---|---|
| DE | 198 45 883 A1 | 5/1999 |
| DE | 0 539 537 | 12/2000 |
| DE | 10 2004 063769 | 7/2006 |
| EP | 0 636 310 | 2/1995 |
| EP | 0 730 164 | 9/1996 |
| EP | 0 750 188 | 12/1996 |
| EP | 0 511 184 | 6/1998 |
| FR | 2549963 | 1/1985 |
| GB | 1355612 | 6/1974 |
| GB | 1408458 | 10/1975 |
| JP | 406284806 A | 10/1994 |
| JP | 10-319106 | 12/1998 |
| WO | WO 96/24830 | 8/1996 |
| WO | WO 97/00887 | 1/1997 |
| WO | WO 98/44140 | 10/1998 |
| WO | WO 99/40419 | 8/1999 |
| WO | WO 99/41383 | 8/1999 |
| WO | WO 99/58959 | 11/1999 |
| WO | WO 00/52990 | 9/2000 |
| WO | WO 00/71993 | 11/2000 |
| WO | WO 01/22043 | 3/2001 |
| WO | WO 01/44828 | 6/2001 |
| WO | WO 01/89288 | 11/2001 |
| WO | WO 02/16090 | 2/2002 |
| WO | WO 02/48687 | 6/2002 |
| WO | WO 02/059586 | 8/2002 |
| WO | WO 02/071040 | 9/2002 |
| WO | WO 03/100381 | 12/2003 |
| WO | WO 2006/026466 | 3/2006 |
| WO | WO 2006/026467 | 3/2006 |

OTHER PUBLICATIONS

"Seed Meister Luminar 3076", Brimrose Corporation of America, Baltimore, MD, http://www.brimrose.com/seed_meister.html; (Jan. 3, 2002).

Archibald et al., "Development of Short-Wavelength Near-Infrared Spectral Imaging for Grain Color Classification," SPIE vol. 3543, pp. 189-198 (1998).

Bauman et al., Inheritance of Variations in Oil Content of Individual Corn (Zea mays L.) Kernels, Crop Science, 5:137-138 (1965).

Daun et al., "Comparison of Three Whole Seed Near-Infrared Analyzers for Measuring Quality Components of Canola Seed", JAOCS, 71(10):1063-1068 (1994).

Delwiche, "Single Wheat Kernel Analysis by Near-Infrared Transmittance: Protein Content," Analytical Techniques and Instrumentation, JAOCS, 72(1):11-16 (1995).

Dowell et al., "Automated Single Wheat Kernel Quality Measurement Using Near-Infrared Reflectance," ASAE Annual International Meeting, paper No. 973022 (1997).

Dowell et al., "Automated Color Classification of Single Wheat Kernels Using Visible and Near-Infrared Reflectance," Cereal Chem 75(1):142-144 (1998).

Dowell, "An Intelligent Automated System for Determining Peanut Quality," IEEE International Workshop on Intelligent Robots and Sytems, IROS, pp. 237-241 (1990).

Dr. Jolanta Soos, "Industrial Process Monitoring Requires Rugged AOTF Tools", Laser Focus World, Aug. 1994.

Gambhir et al. "Simultaneous Determination of Moisture and Oil Content in Oilseeds by Pulsed Nuclear Magnetic Resonance," JAOCS, 62(1):103-108 (1985).

Halloin et al. "Proton Magnetic Resonance Imaging of Lipid in Pecan Embryos," JAOCS, 70(12):1259-1262 (1993).

Heil et al. "Magnetic Resonance Imaging and Modeling of Water Up-take into Dry Beans," Lebensm-Wiss u-Technol, 25:280-285 (1992).

Lakshminarayana et al. "Spatial distribution of oil in groundnut and sunflower seeds by nuclear magnetic resonance imaging," J. Biosci 17(1):87-93 (1992).

MacNamara et al., "Multiplex sample NMR: an approach to high-throughput NMR using a parallel coil probe," Analytica Chimica Acta, 397:9-16 (1999).

Massie, et al. "Spectral Reflectance and Transmittance Properties of Grain in the Visible and near Infrared", Transactions of the ASAE, Winter Meeting of the American Society of Agricultural Engineers, pp. 598-600 (1965).

McEntyre et al., "Comparison of Water Absorption Patterns in Two Barley Cultivars, Using Magnetic Resonance Imaging," *Cereal Chem.*, 75(6):792-795 (1998).

McGinty et al. "A System for Automatic Weight Determination of Individual Grain Kernels: Principles and Evaluation," *Cereal Chem.* 19(5):196-199 (1974).

Orman, et al. "Comparison of Near-Infrared Spectroscopy Calibration Methods for the Prediction of Protein, Oil, and Starch in Maize Grain," *J. Agric. Food Chem.* 39:883-886 (1991).

P.A. Hailey, "The Role of NIR Spectroscopy in the Measurement of Pharmaceutical Manufacture", http://wwwbrimrose.com/hailey.html; (Jan. 2, 2002).

Paige et al. "Apparatus for Automatic Measurement of Kernel Weight, Length, and Thickness," *Crop Sci.* 31:1314-1318 (1991).

Robutti, "Maize Kernel Hardness Estimation in Breeding by Near-Infrared Transmission Analysis," *Cereal Chem* 72(6): 632-636 (1995).

Rubel et al. "Simultaneous Determination of Oil and Water Contents in Different Oilseeds by Pulsed Nuclear Magnetic Resonance," *JAOCS* 71(10):1057-1062 (1994).

Saito et al. "Application of Magnetic Resonance Imaging to Non-Destructive Void Detection in Watermelon," *Cryogenics* 36(12):1027-1031 (1996).

Sander et al., "System for Automatic Weight Determination of Individual Grain Kernels," *Transactions of the ASAE*, pp. 1146-1147 (1973).

Siebenmorgen et al. "A Data Acquisition/Control System for Individual Kernel and Thin-Layer Grain Drying Research" *Am. Soc. Of Agri. Engrs., Univ. of Ark., 1991 Int'l Summer Meeting, Paper 91-3042*, pp. 1-16 (1991).

Song et al., "Non-invasive Measurement of Moisture Distribution in Individual Wheat Kernels by Magnetic Resonance Imaging," *SPIE*, 2345:414-422 (1994).

Yoshida et al., "An automatic sequential single-seed weighing system: variation in soybean seed weight," *J. Fac. Agr. Hokkaido Univ.* 61(2):225-232 (1982).

Pioneer Hi-Bred International, Inc., Downloadable Photos—Laser-Assisted Seed Selection, http://www.pioneer.com/web/site/portal/menuiteam.b9e99dcb8e2cfd8ecfe6d10093a0/, printed as of Nov. 25, 2008, 4 pages.

Been et al., "A scaled-up Seinhorst elutriator for extraction of cyst nematodes from soil" Nematology, vol. 9, No. Part 3, pp. 431-435, (Mar. 2007).

Winfield et al., "A column elutriator for extracting cyst. Nematodes and other small invertebrates from soil samples", Annals of Applied Biology, vol. 111, No. 1, pp. 223-232 (1987).

\* cited by examiner

HIGH THROUGHPUT AUTOMATED SEED ANALYSIS SYSTEM

CROSS REFERENCE TO RELATED APPLICATIONS

The present application is related to U.S. application for Ser. Nos. 10/406,910 (now U.S. Pat. No. 7,044,306), 09/739,871 and 09/698,214 (now U.S. Pat. No. 6,646,264), the disclosures of which are hereby incorporated by reference.

BACKGROUND OF THE INVENTION

1. Technical Field of the Invention

The present invention relates to a system that is operable to pick individual seeds from a bin, place those seeds in a divided tray, image the seeds, and then sort the seeds for further processing.

2. Description of Related Art

In the agricultural industry, and more specifically in the seed breeding industry, it is important for scientists to be able to analyze seeds with high throughput. By this it is meant that the analysis of the seeds preferably occurs not only quickly, but also with high total volume. Historically, however, seed analysis has been a tedious, manual task requiring individual manipulation of seeds. Such seeds are examined, weighed, imaged (with the image data being analyzed), and then sorted. This task is suitable to automation, and the present invention addresses the need for a high throughput automated seed analysis system.

SUMMARY OF THE INVENTION

The present invention is a device that includes a transport subsystem for conveying trays between a plurality of stations. A loading subsystem is positioned at a first station and is operable to load seeds into individual wells of the tray. An imaging subsystem is positioned at a second station and is operable to image the seeds contained within the tray wells. A sorting subsystem is positioned at a third station and is operable to remove the seeds from the tray wells and sort the removed seeds into a plurality of sort bins.

In one embodiment of the invention, a processing functionality analyzes the seed images and makes a sorting determination with respect to the seeds on the tray based on the seed analysis processing. In this regard, the processing functionality determines from the analysis of the seed images the one of the plurality of bins into which each seed should be directed by the sorting subsystem.

In another embodiment of the invention, the transport subsystem comprises a turntable conveyance device. Such a device advantageously allows for easy recirculation of the trays in the system.

In another embodiment of the invention, the loading subsystem includes a mechanism for picking individual seeds from an input bin and placing those picked seeds at the well locations on the tray.

In another embodiment of the invention, the imaging subsystem comprises one of a visible light imager, a near infrared light imager, or an NMR/MRI imager.

In another embodiment of the invention, the sorting subsystem includes a pneumatic suction device for selectively removing individual ones of the seeds from wells in the tray and a diverting mechanism for directing the removed seed(s) to a certain one of the sort bins.

BRIEF DESCRIPTION OF THE DRAWINGS

A more complete understanding of the method and apparatus of the present invention may be acquired by reference to the following Detailed Description when taken in conjunction with the accompanying Drawings wherein.

DETAILED DESCRIPTION OF THE PREFERRED EMBODIMENTS

Figure 1:
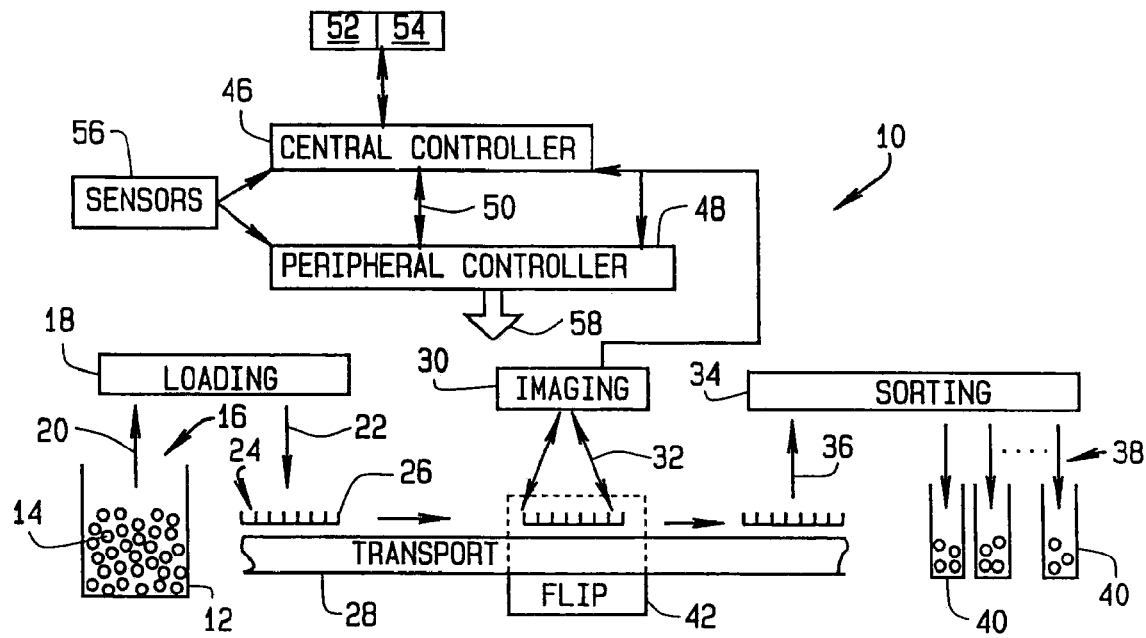
FIG. 1 is a functional block diagram of a seed analysis system in accordance with the present invention.

Reference is now made to FIG. 1 wherein there is shown a functional block diagram of a seed handling system 10 in accordance with the present invention. An input bin 12 is sized to hold a large number of individual seeds 16 (for example, tens to thousands, or more). A loading subsystem 18 operates to pick 20 individual ones 14 of the seeds 16 from the bin 12, and then transfer 22 those picked seeds to individual well locations 24 in a divided tray 26. The divided tray 26 is then transported by a transport subsystem 28 from the area of the loading subsystem 18 (i.e., a loading station) to the area of an imaging subsystem 30 (i.e., an imaging station) where images 32 of the seeds 16 in the divided tray 26 are obtained. These images 32 may comprise visual images, near infra-red images or NMR/MRI images, in accordance with the type of imager which is utilized by the imaging subsystem 30. Following imaging, the divided tray 26 is further transported by the transport subsystem 28 from the area of the imaging subsystem 30 to the area of a sorting subsystem 34 (i.e., a sorting station) where individual ones 14 of the seeds 16 contained in well locations 24 of the divided tray 26 are selectively picked 36 and then delivered 38 to individual sort bins 40. In this context, it is envisioned that the sorting determination (i.e., into which bin 40 each seed 16 is delivered) is driven by an analysis performed on the seed images 32 obtained by the imaging subsystem 32. It is further possible for the sorting determination to be made using some other factor or consideration as selected by the user.

As an optional component, the system 10 may further including a flip subsystem 42 which is positioned in the area of the imaging station, and operates in conjunction with the imaging subsystem 30. The flip subsystem 42 functions to flip the seeds 16 such that the imaging subsystem 30 can obtain multiple images of each seed, where these images are preferably of opposite seed sides. For example, take corn seeds which generally possess two, generally opposing, flat sides. When deposited 22 in the tray 26, the corn seeds 16 will come to rest with one of their flat sides down, and the image obtained will be of the seeds with this orientation. The obtained image data for the seeds can be enhanced, however, if images of each side of the seed were obtained (i.e., a first image with the first flat side down, and a second image with the second, opposed, flat side down). The flip subsystem 42 facilitates this enhanced image data acquisition operation by turning the seeds 16 which are present in the tray 26 over to allow for a second image 32 to be taken before the transport subsystem 28 moves the tray 26 on to the sorting subsystem 34.

The operation of the system 10 is preferably completely automated. More specifically, the operations performed by the loading subsystem 18, transport subsystem 28, imaging subsystem 30 and sorting subsystem 34 preferably occur substantially without need for human interaction, intervention or control. It is also possible for any needed actions to load the seeds 16 into the input bin 12 and/or physically manipulate and change the sort bins 40 (either individually or collectively) where sorted individual ones 14 of the seeds 16 are deposited, to be automated as well. These actions, however, are generally done manually with human participation without detracting from the improved performance obtained by the system 10.

To effectuate this automated operation over all or substantially all of the system 10, a central controller 46 is included that may comprise a specially programmed computer and associated peripheral devices that enable communication with, and control over the operations of, the various components of the system 10. As an example, the central controller 46 may comprise a PENTIUM® class personal computer running a WINDOWS® based operating system with a custom C++ application executing to control component operations. Use of the PENTIUM/WINDOWS combination opens the door for the use of other custom or commercial (off-the-shelf) applications in conjunction with the control operation application to exchange data (for example, use of spread sheet or report generating applications to output seed data and images to the user).

A peripheral controller 48, connected to the central controller 46, interfaces with the system 10 components, and directs, under the instruction of the central controller pursuant to the executing custom application, system component operation. For example, the peripheral controller 46 may function to control the operation of each of the loading subsystem 18, transport subsystem 28, imaging subsystem 30, sorting subsystem 34 and flip subsystem 42, both individually and in a coordinated effort with each other. The peripheral controller 48 may comprise a universal motion controller such as a PARKER 6K controller manufactured by the Compumotor Division of Parker Hannifin Corp. The connection 50 between the peripheral controller 48 and the central controller 46 may comprise any network-based type connection and more specifically may utilize an ethernet 10-base T connection, or the like.

In addition to storing programming for controlling system 10 operation, the memory (or other data storage functionality, not explicitly shown but inherently present) provided within the central controller 46 is used to store the images and related image data (collectively, data 52) relating to individual ones 14 of the seeds 16 in a database or other suitable format. This data 52 is collected from the imaging subsystem 30 operation and is delivered to the central controller 46 for storage and/or manipulation, as necessary. Still further, the memory of the central controller 46 may also obtain data 54 that is received from, or is derived in connection with controlling the operation of, the sorting subsystem 34 concerning the bins 40 where individual ones 14 of the seeds 16 have been deposited 38. Preferably, this location data 54 is correlated in the database or other format with the image data 52 on an individual seed-by-seed basis.

The system 10 further includes a number of sensors 56 that operate to detect conditions of interest in the system and report that information to either or both the central controller 46 and/or the peripheral controller 48. With this information, the central controller 46 and the peripheral controller 48 exercise control (generally illustrated by arrow 58) over the operations and actions taken by the various components of the system 10. For example, the sensed condition information may concern: the successful picking 20 of individual ones 14 of the seeds 16 from the bin 12; the positioning of the loading subsystem 18; the positioning of the tray(s) 26; the operation of the transport subsystem 28; the operation of the flip subsystem 42; the direction of deposit 38 performed by the sorting subsystem 34; the status (for example, position, location, vacuum, pressure, and the like) of various component parts of the subsystems; operation, maintenance, performance, and error feedback from the various components of the system (separate from, or perhaps comprising or in conjunction with, collected data 52/54); and the like. More specifically, sensor information that is collected and processed for use in controlling system operation may include information like: device or component status; error signals; movement; stall; position; location; temperature; voltage; current; pressure; and the like, which can be monitored with respect to the operation of each of the components (and parts thereof) within the system 10.

Figures 2A, 2B:
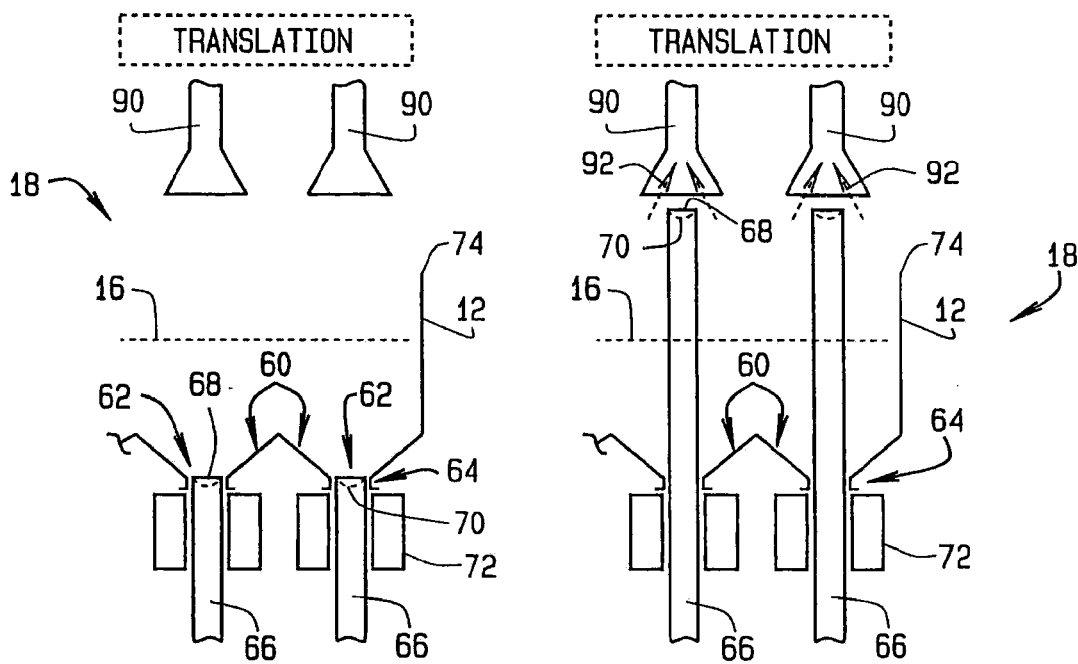
FIGS. 2A and 2B are schematic side views of one embodiment for a picking portion of the loading subsystem utilized within the system of FIG. 1.

Reference is now made to FIGS. 2A and 2B wherein there are shown schematic side views of one embodiment for a picking portion of the loading subsystem 18 utilized within the system of FIG. 1. As can be seen, the input bin 12 includes a plurality of concave-shaped (inwardly sloped) bottom portions 60. These sloped portions serve to direct individual ones of the seeds 16, through the force of gravity, toward the bottom 62 of the input bin 12 as seeds are picked therefrom, and thus enhance the likelihood of picking each seed contained within the input bin. At the bottom 62 of each concave-shaped portion 60 is an opening 64. Positioned within each opening 64 is a linear air piston 66. When positioned in an un-actuated position (shown in FIG. 2A), end 68 of the piston 66 is located such that it is substantially flush with the bottom 62 at the opening 64. It will be recognized that "substantially flush" in this context includes a position slightly below the bottom 62 where the opening 64 may act to hold or funnel an individual piece for subsequent capture by the piston 66 as described below. The end 68 of the piston 66 is further provided with a concave depression 70 (illustrated in dotted lines) whose perimeter is slightly smaller than the outer diameter of the piston 66 itself. The perimeter of the depression 70 is sized, generally speaking, to be commensurate with, and more particularly, slightly larger than, the expected average size of the individual ones of the seeds 16 to be contained within the bin 12 and handled by the system 10. This allows for the handling of individual seeds of non-uniform size/shape. An air drive 72 operates under the control of the peripheral controller 48 and central controller 46 (see, FIG. 1) to linearly move the piston 66 between the un-actuated location shown in FIG. 2A and the actuated location shown in FIG. 2B. Although an air drive 72 is shown for each piston 66, it will be understood that a single air drive could be configured to simultaneously actuate each of the plurality of pistons. When moving towards the actuated location (FIG. 2B), the concave depression 70 at the end 68 of the piston 66 captures an individual one 14 of the seeds 16 from the collected mass of seeds in the bin and raises that seed above the bottom portion to a location at or about a top edge 74 of the bin 12.

Once an individual seed 16 has been raised to the top edge 74, it is necessary to remove the individual piece from the end of the piston 66 for further handling. The picking portion further includes a plurality of vacuum cups 90 arranged and oriented to correspond with the plurality of pistons 66. The air drive 72 linearly moves the pistons 66 from the un-actuated location to the actuated location shown where the captured seed on each piston is positioned adjacent a corresponding one of the vacuum cups 90. More specifically, in a preferred embodiment, each piston 66 is raised into the actuated location to place its captured seed 16 in contact with one of the vacuum cups 90. To minimize the likelihood of damage caused by such contact, each vacuum cup 90 is preferably spring loaded and thus will give in response to contact caused by the raising of the captured seed. At that point, a slight vacuum is drawn (dotted arrows 92; under the control of the peripheral controller 48 and central controller 46) to hold the seed within the vacuum cup 90. This vacuum may be drawn using Venturi forces in a manner well known in the art. The piston 66 is then returned to the un-actuated location shown in FIG. 2A (and is thus positioned to start the process for picking a next individual seed).

Figure 3A:
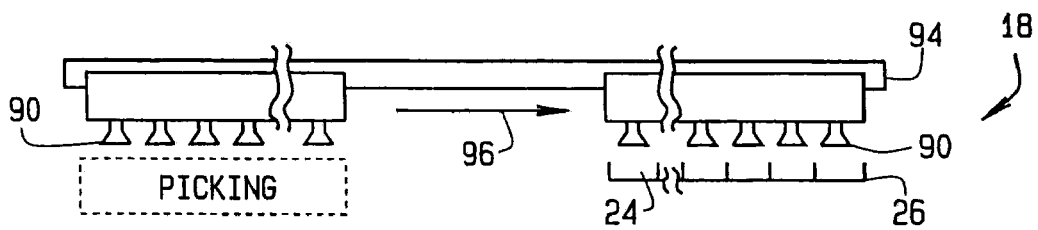
FIGS. 3A-3B are schematic side views of embodiments for a translation portion of the loading subsystem utilized within the system of FIG. 1.
Figure 3B:
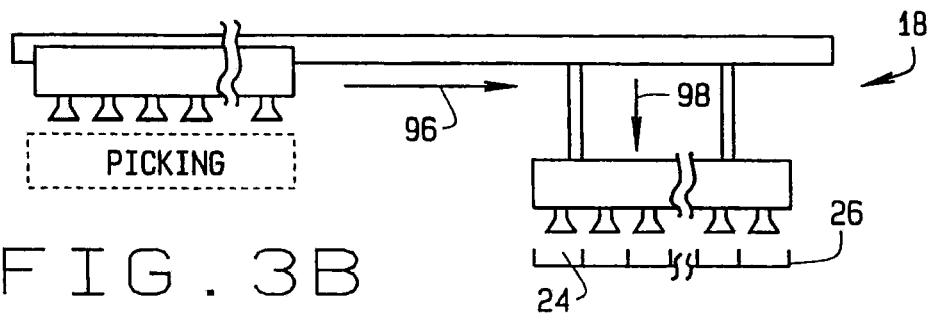

Reference is now made to FIGS. 3A-3B wherein there is shown a translation portion of the loading subsystem 18 utilized within the system of FIG. 1. The individual seeds 16 held by the vacuum cups 90 are now ready to be delivered for further processing. A translation stage 94 moves the plurality of vacuum cups 90 (each holding a seed 16) under the control of the peripheral controller 48 and central controller 46 in a horizontal direction 96 (FIG. 3A) in order to clear the input bin 12 and be placed into a position above the tray 26 on the transport subsystem 28 (see, also, FIG. 1). Each vacuum cup 90 in the picking portion, under the control of the peripheral controller 48 and central controller 46, then releases its held seed 16 (perhaps using a positive pressure 94, in addition to gravitational force, under the control of the peripheral controller 48 and central controller 46) so as to deposit the seeds in the divided tray 26 well locations 24.

In an alternative embodiment, the translation stage 94 may additionally move under the control of the peripheral controller 48 and central controller 46 from its FIG. 3A position in a vertical direction 98 (FIG. 3B) to position each of the vacuum cups 90 over a corresponding one of the well locations 24 of the divided tray 26. Such an embodiment would be necessary when the transport subsystem 28 could not be positioned to receive the seeds directly following the horizontal movement 96 shown in FIG. 3A. For example, such a lowering operation as performed by the translation stage 94 would be necessary when concerns exist over sliding the held seeds across and over the top of the tray 26 or when the transport subsystem 28 is required to be located below the loading subsystem 18. Each vacuum cup 90 in the picking portion, under the control of the peripheral controller 48 and central controller 46, then releases its held seed 16 (perhaps using a positive pressure 94, in addition to gravitational force, under the control of the peripheral controller 48 and central controller 46) so as to deposit the seeds in the divided tray 26 well locations 24.

It will be understood that the loading subsystem 18 preferably includes the same number of vacuum cups 90 (having the same arrangement) as the divided tray 26 has well locations 24. For example, if the divided tray has 24 well locations in a 4×6 array format, then the loading subsystem 18 should correspondingly have 24 vacuum cups 90 also in a 4×6 array format. In this way, one divided tray 26 can be fully loaded with seeds using a single actuation of the loading subsystem 18 under the control of the peripheral controller 48 and central controller 46 (i.e., a single actuation of the picking portion followed by a single actuation of the translation portion).

Alternatively, the loading subsystem 18 could possess an even submultiple number of vacuum cups 90 (having a submultiple arrangement) as the divided tray 26 has well locations 24. For example, if the divided tray has 96 well locations in a 16×24 array format, then the loading subsystem 18 could correspondingly have 24 vacuum cups 90 in a 4×6 array format. In this way, one divided tray 26 can be fully loaded with seeds using four consecutive actuations of the loading subsystem 18 under the control of the peripheral controller 48 and central controller 46 (as described above). Appropriate x-y translation by the translation stage 94 may be used to accurately position the cups 90 for each consecutive seed deposit.

Figure 9A:
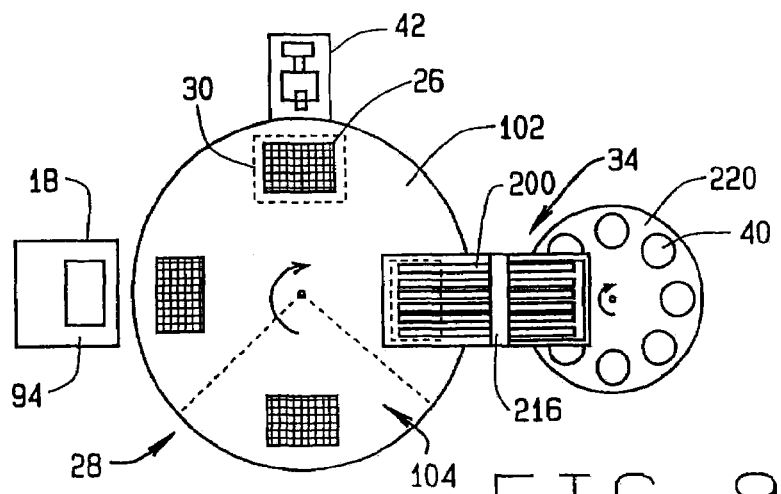
FIGS. 9A and 9B are top and perspective views, respectively, of the seed handling system utilizing the subsystems disclosed herein.
Figure 9B:
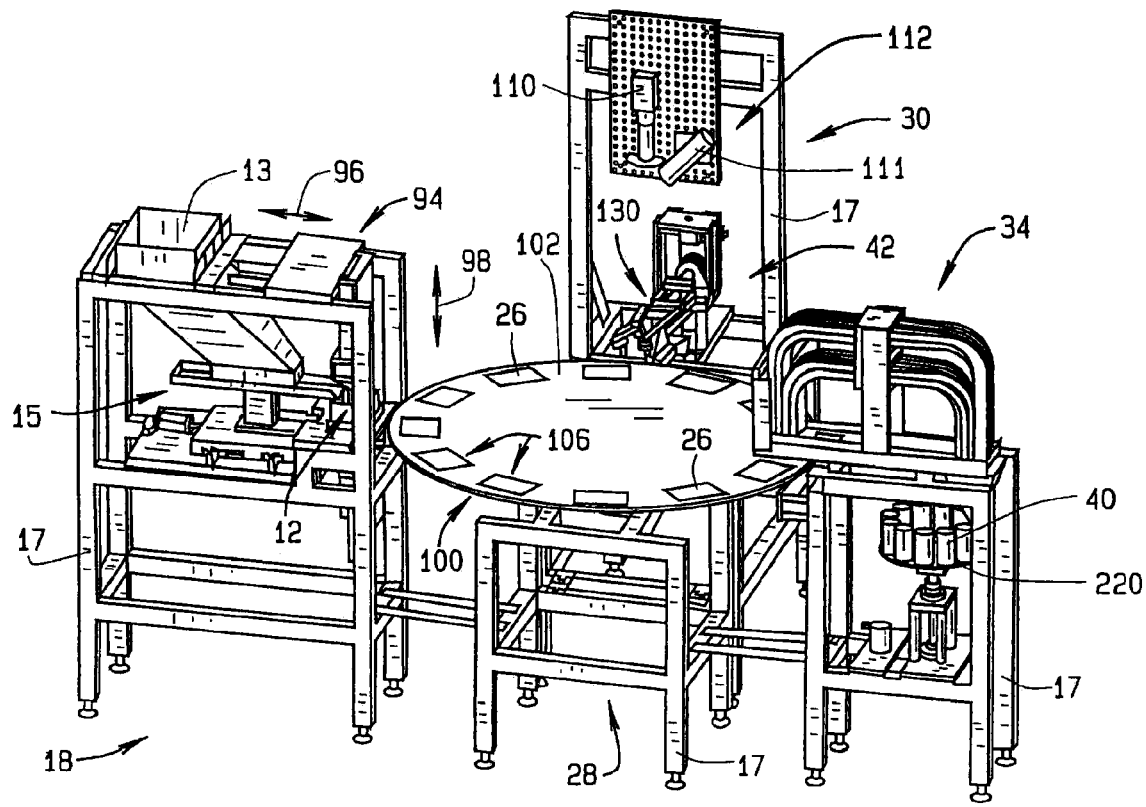
Figure 9F:
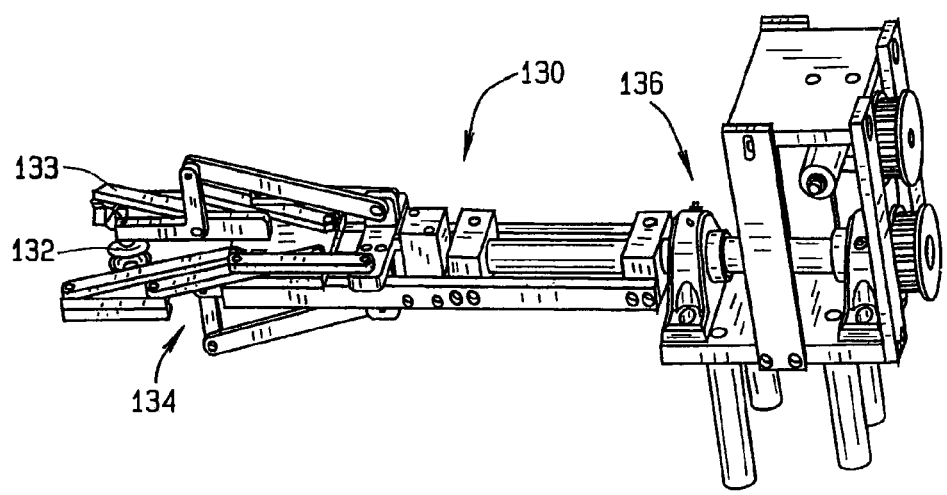
FIG. 9F is a perspective view of the arm for the flip subsystem.
Figure 9C:
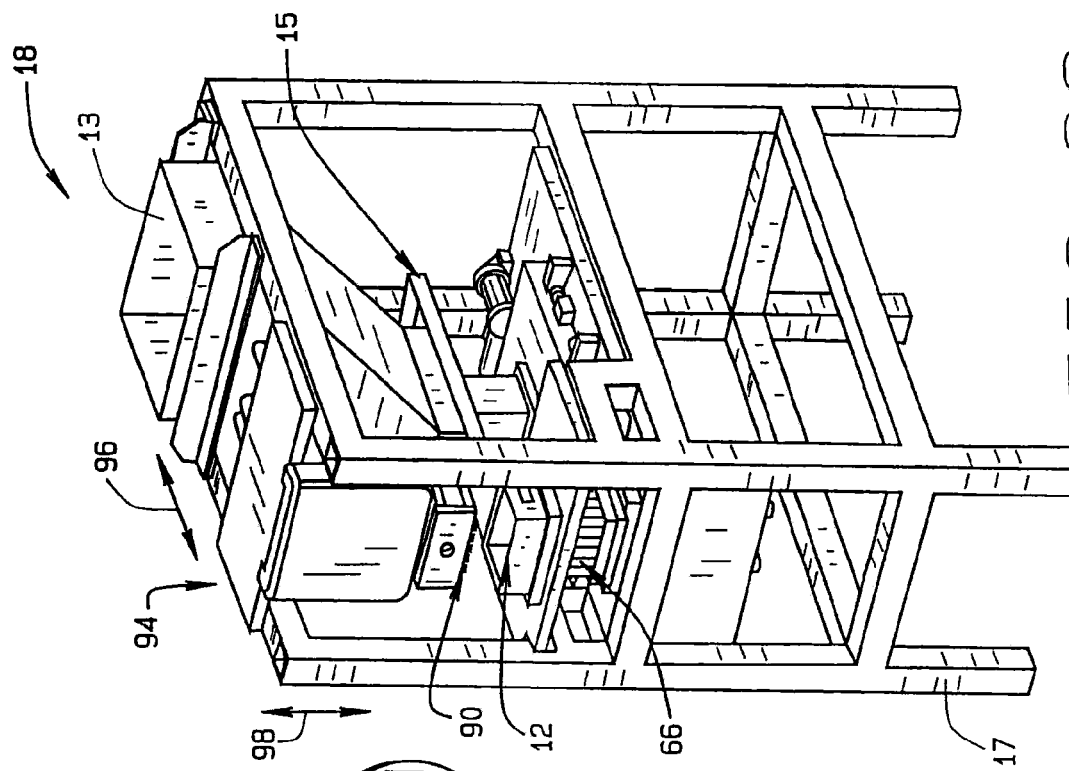
FIG. 9C is a perspective view of the loading subsystem.

Perspective views of a preferred implementation of the loading subsystem 18 are shown in the system 10 illustration of FIG. 9B and in FIG. 9C. FIGS. 9B and 9C provide further detailed information concerning the loading subsystem 18 implementation. For example, in connection with the input bin 12, a loading hopper 13 is positioned to receive bulk seeds at its input. These seeds are delivered by the hopper 13 to an inclined vibrating tray assembly 15. Actuation of the assembly 15 causes seeds received from the output of the hopper 13 to be delivered in a controlled manner to the input bin 12.

FIGS. 9B and 9C further illustrate additional details concerning the translation stage 94 in that it includes both a horizontal actuator 94h (providing the movement 96) and a vertical actuator 94v (providing the movement (98).

As also shown in FIGS. 9B and 9C, a frame 17 is provided to support the various component parts of the loading subsystem 18 and facilitate its interconnection with other subsystems of the system 10.

Figure 4:
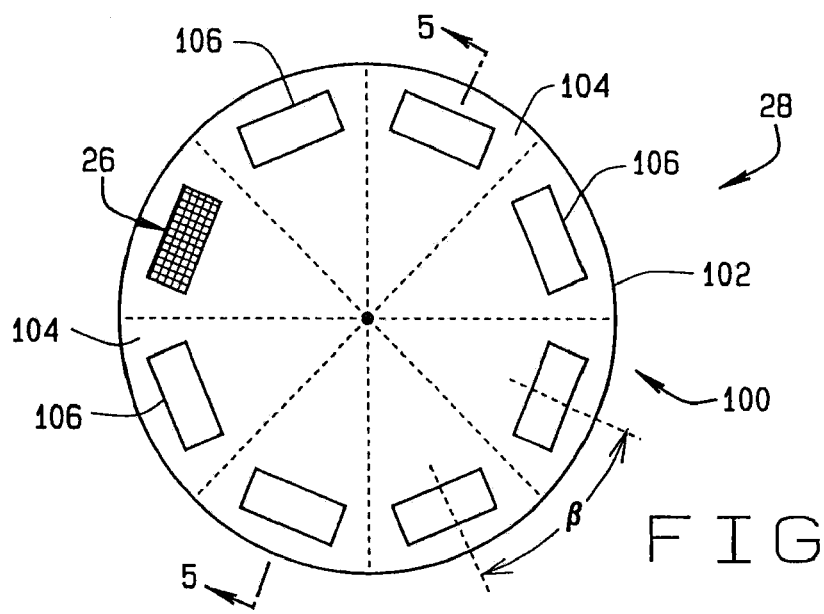
FIG. 4 is a top view of the transport subsystem utilized within the system of FIG. 1.

Reference is now made to FIG. 4 wherein there is shown a top view of the transport subsystem 28 utilized within the system of FIG. 1. Generally speaking, the transport subsystem 28 can be any suitable conveyance mechanism such as, for example, a belt conveyor, roller conveyor, and the like. In a preferred embodiment of the invention, however, the transport subsystem comprises a turntable conveyor 100. The conveyor 100 includes a round, turntable support 102 that is pivotally mounted at its center for rotation. The turntable support 102 is virtually divided into a plurality of pie-shaped sectors 104, with each sector including a cut-out 106 sized and shaped to receive and support a divided tray 26 (only one shown, see, also, FIG. 1). The number of sectors 104 available on the turntable support 102 may be even or odd with a number chosen which depends in large part on the diameter of the support, the size of the tray 26 and the needs of the transport application.

Figure 5:
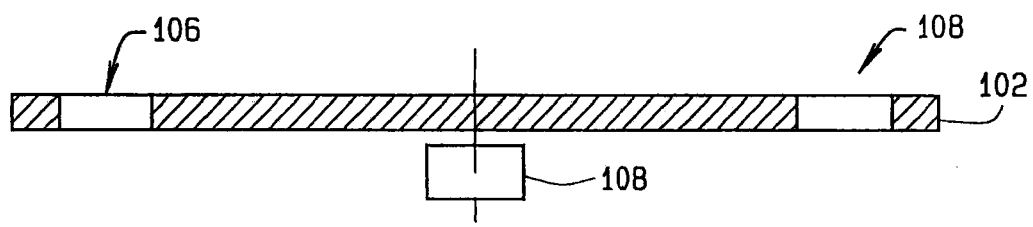
FIG. 5 is a schematic diagram of the imaging subsystem utilized within the system of FIG. 1.

Reference is now made to FIG. 5 wherein there is shown a cross-sectional illustration of the transport subsystem 28. As discussed above, the circular turntable support 102 is pivotally mounted at its center to a shaft and bearing system. This shaft may comprise the output shaft of an actuating motor 108

(as shown), or alternatively may be separate from the actuating motor with the turntable shaft being driven for rotation by a suitable chain drive, pulley drive or gear drive. The actuating motor 108 is preferably a high torque stepper motor.

In operation, the actuating motor 108 for the turntable support 102 is actuated under the control of the peripheral controller 48 and central controller 46 to step forward (which can be either clockwise or counter clockwise, depending on configuration) enough times cause one sector's worth of rotational movement. In other words, with each actuation of the motor, the turntable support 102 rotates an angular amount equal to the angle β between two consecutive cut-outs 106. In this way, very precise advances in turntable rotation are made from station to station and alignment with auxiliary devices (such as the loading subsystem 18 described above) at certain station locations can be made. In this configuration, an auxiliary device can be positioned about the turntable support at stations which are in alignment with each sector 104 position and thus have precise access to the cut-outs 106, the trays 26 held therein, and the wells 24 within each held tray.

In the event a stepper-type motor is not used, a conventional motor may be used in conjunction with a sensor 56 (perhaps an indexing sensor) to detect rotational advancement of the turntable support 102 by the angle β so as to align with a station.

To the extent necessary, the peripheral edges of the turntable support 102 may be supported with rollers, guides, slides, or the like, to assist with smooth rotation of the turntable conveyor 100.

Figure 9D:
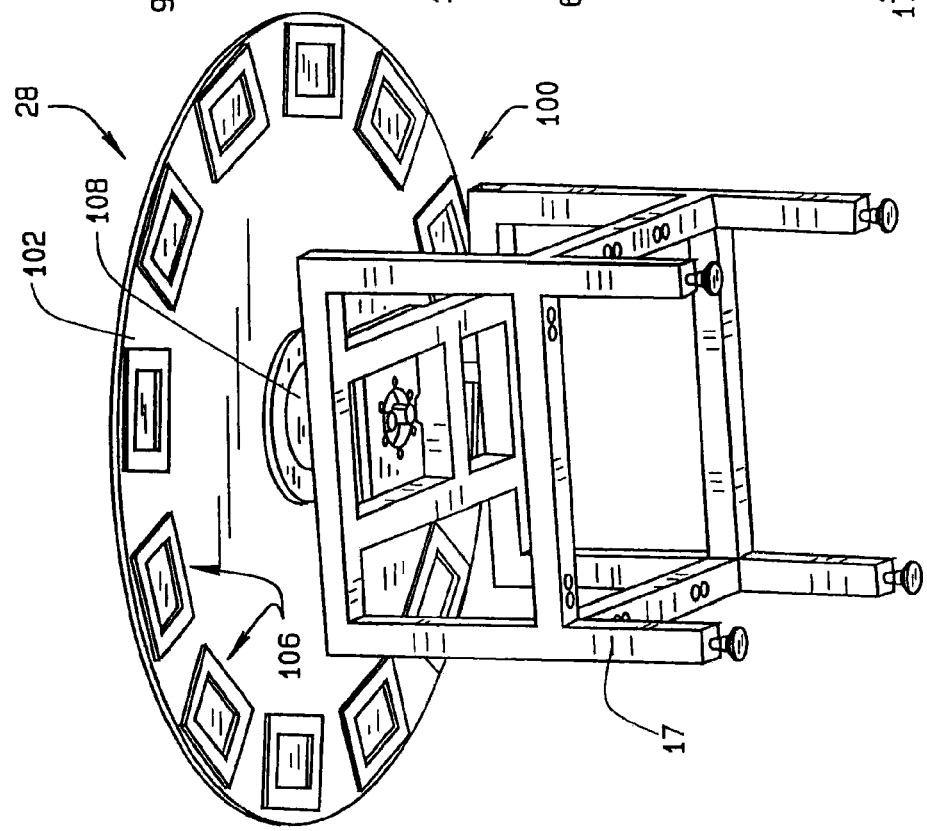
FIG. 9D is an underside perspective view of the transport subsystem.

Perspective views of a preferred implementation of the transport subsystem 28 are shown in FIGS. 9B and 9D. FIGS. 9B and 9D provide further detailed information concerning the transport subsystem 28 implementation using a turntable conveyor 100. For example, a frame 17 is provided to support the various component parts of the transport subsystem 28 and facilitate its interconnection with other subsystems of the system 10.

Figure 6:
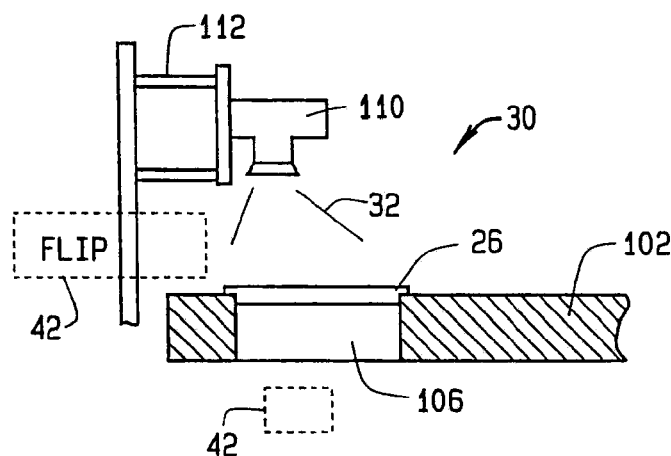
FIG. 6 is a schematic diagram of the imaging subsystem utilized within the system of FIG. 1

Reference is now made to FIG. 6 wherein there is shown a schematic diagram of the imaging subsystem 30 utilized within the system of FIG. 1. The imaging subsystem 30 includes a camera 110 mounted to a support bracket 112. The support bracket 112 facilitates aiming of the camera 110 at the transport subsystem 28 where trays 26 are positioned for imaging. More specifically, with reference to the preferred implementation of the transport subsystem 28 as shown in FIGS. 4-5, the support bracket 112 allows for the camera 110 to be accurately aimed, with the proper angle, at the area of the sector 104 of the turntable support 102 where the cut-outs 106 holding seed filled trays 26 are located with each successive rotational advancement.

The camera 110 may be any suitable imaging camera selected in accordance with the imaging goals of the analysis application for the seeds. For example, in connection with an analysis for external seed coat damage, the camera may comprise a camera operable in the visible range. Alternatively, for internal seed analysis, the camera may comprise a camera operable in the near infra-red range (see, U.S. application for patent Ser. No. 09/698,214, the disclosure of which is hereby incorporated by reference). Still further, the camera may comprise a camera which implements NMR/MRI imaging techniques (see, U.S. application for patent Ser. No. 09/739,871, the disclosure of which is hereby incorporated by reference).

The image data collected by the camera 110 (visible, infrared, NMR/MRI, or the like) is correlated with particular seeds (more specifically, to certain well locations in the tray where those seeds are contained). In this way, a link exists between the image data and a seed. The image data may be processed in a number of known ways (like those detailed in the '214 and '871 applications referenced above) to identify seed characteristics. For example, image data analysis may reveal characteristic information of the individual seeds concerning, for example, the presence/absence of biochemical traits (like oil content), the presence/absence of damage, the presence/absence of disease, size, color, shape and the like. This characteristic information is obtained by processing the image data using custom algorithms executed on the data by the central controller 46. The results of this processing are then stored in correlation with particular seeds (more specifically, with certain well locations in the tray where those seeds are contained). In this way, a link exists between the image data/characteristic information and a seed. As will be discussed herein, the characteristic data can then be applied by the central controller 46 against certain sorting criteria in order to effectuate the sorting of the seeds by characteristic.

Figure 9E:
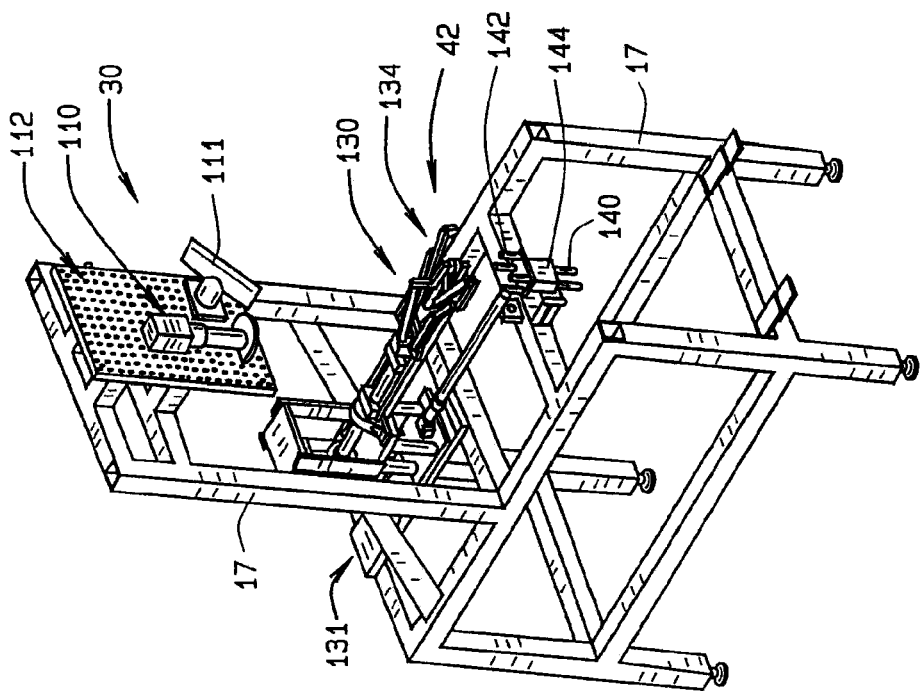
FIG. 9E is a perspective view of the imaging subsystem and flip subsystem.

Perspective views of a preferred implementation of the imaging subsystem 30 are shown in FIGS. 9B and 9E. FIGS. 9B and 9E provide further detailed information concerning the imaging subsystem 30 implementation using a camera 110. For example, a frame 17 is provided to support the various component parts of the imaging subsystem 30 and facilitate its interconnection with other subsystems of the system 10. The frame 17 and the support bracket 112 allow the camera 110 to be cantilevered out such that it can be positioned over the transport subsystem 28. The bracket 112 further supports the making of positioning and aiming adjustments with respect to the camera 110 and any related devices (such as an illuminating lamp 111).

Figure 7A:
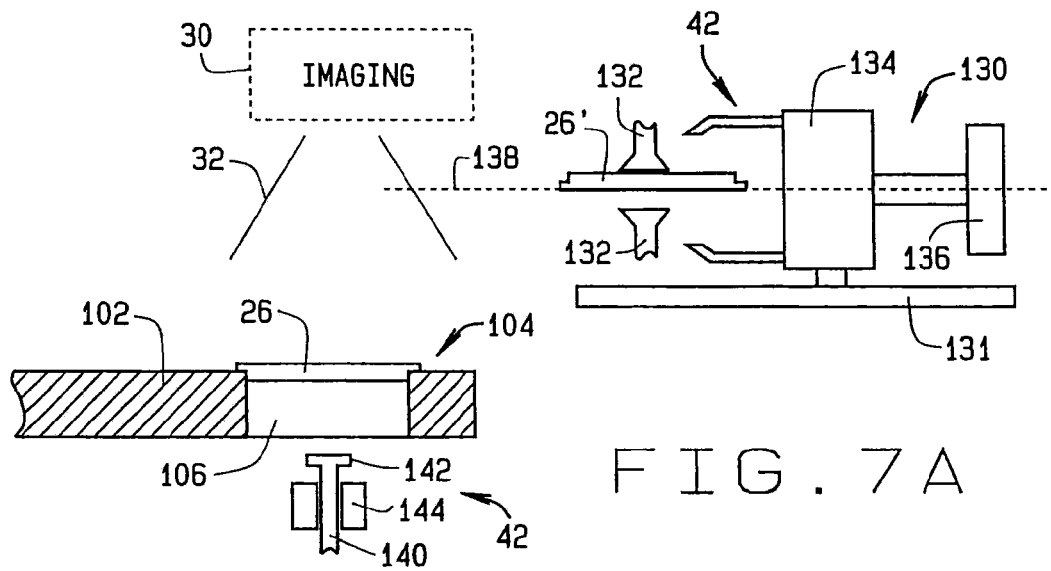
FIGS. 7A-7D are schematic side views of one embodiment for the flip subsystem utilized within the system of FIG. 1.
Figure 7B:
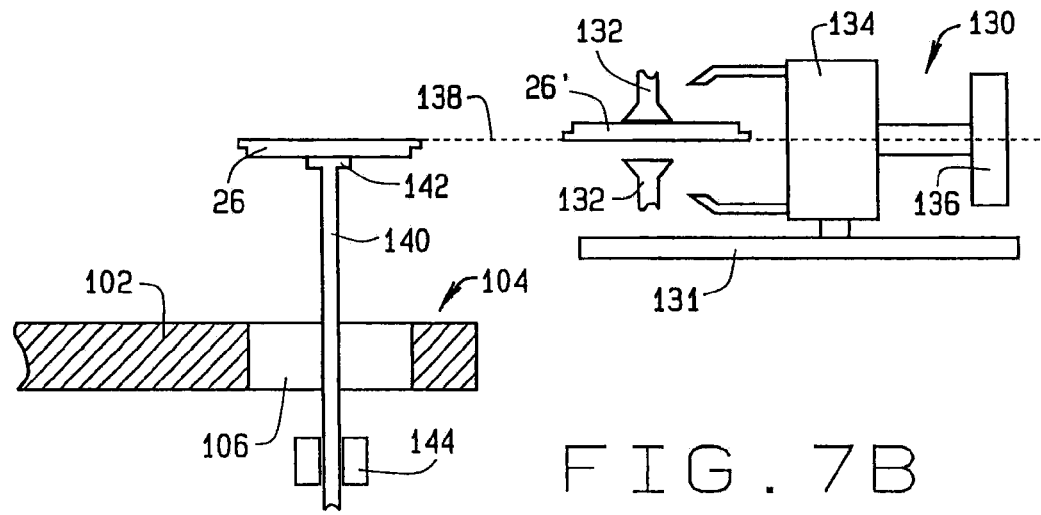
Figure 7C:
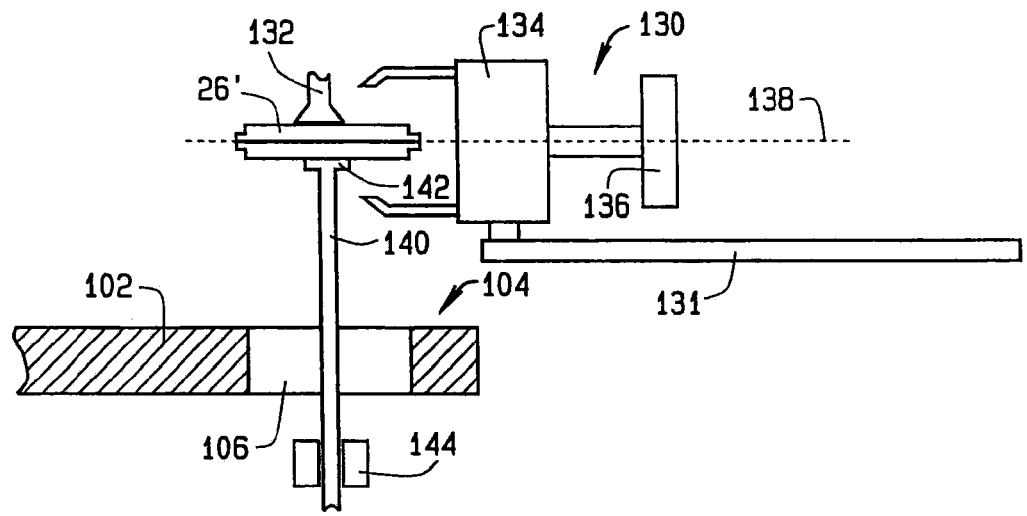

Reference is now made to FIGS. 7A-7D wherein there are shown schematic side views of one embodiment for the flip subsystem 42 utilized within the system of FIG. 1. FIGS. 6 and 7A further illustrate a potential positional relationship between the flip subsystem 42 and the imaging subsystem 30. An arm 130 is movable by a translation stage 131 between a retracted position and an extended position under the control of the peripheral controller 48 and central controller 46 (see, FIG. 1). The arm 130 includes a pair of suction cups 132 and a gripper 134. A drive motor 136 is operable under the control of the peripheral controller 48 and central controller 46 (see, FIG. 1) to rotate the arm 130 in 180° increments about its longitudinal axis 138. The arm 130 is mounted such that it can be positioned, when in the extended position, in the area of the sector 104 of the turntable support 102 where the cut-outs 106 holding seed filled trays 26 are located with each successive rotational advancement. When in the retracted position, however, the arm 130 is moved out of (away from) the sector area of the turntable support 102. Even more particularly, because the flip subsystem 42 is positioned in the area of, and operates in conjunction with, the imaging subsystem 30, the arm 130 is positioned such that it will not interfere with the imaging operations being performed by the imaging subsystem (see, FIG. 7A).

The flip subsystem 42 further includes a linear air piston 140 which is generally located in alignment with the location of the imaging subsystem 30 (see, FIG. 1). More specifically, the piston 140 is located such that it is aligned with a center of the area of the sector 104 of the turntable support 102 where the cut-outs 106 holding seed filled trays 26 are located with each successive rotational advancement. When positioned in an un-actuated position (shown in FIG. 7A), end 142 of the piston 140 is located such that it is below the transport subsystem 28. More specifically, the end 142 would be below the turntable support 120 and any tray 26 held thereby. An air drive 144 operates under the control of the peripheral controller 48 and central controller 46 (see, FIG. 1) to linearly move the piston 140 between the un-actuated position shown in FIG. 7A and the actuated position shown in FIG. 7B. When moving towards the actuated position (FIG. 7B), the end 142 of the piston 140 passes through the cut-out 106 in the turntable support 102 to raise a tray 26 above the top surface of the transport subsystem 28. When the piston 140 returns to the un-actuated location, a tray 26 is lowered back into position in the cut-out 106.

An upper one of the suction cups 132 holds, at the direction of the peripheral controller 48 and central controller 46, an empty tray 26' in an upside-down orientation. At the appropriate time, following actuation of the piston 140 to lift the seed-filled tray 26 above the transport subsystem 28 (FIG. 7B), the peripheral controller 48 and central controller 46 move the arm 130 to the extended position (FIG. 7C) such that the empty tray 26' is positioned above the tray 26 raised above the transport subsystem 28 which is filled with seeds 16. In this position, the trays 26 and 26' are in effect stacked facing each other and are aligned. The peripheral controller 48 and central controller 46 then causes the gripper 134 to clamp down on the two facing trays. At any suitable time, suction on the tray 26 can be released by the upper suction cup 132. As a result of the clamping action, a plurality of cavities (formed by opposed wells) are created between the two stacked facing plates to hold the seeds while the flipping action subsequently takes place. The piston 140 is then withdrawn by the peripheral controller 48 and central controller 46 back to the un-actuated location so that it is not in the way of further processing of the trays (FIG. 7D).

Figure 7D:
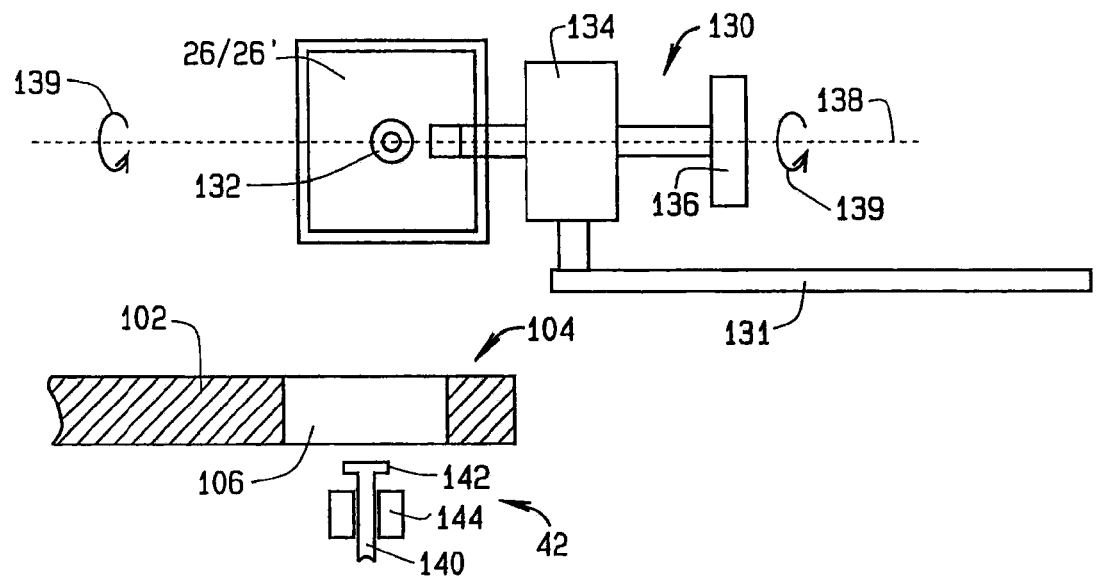

Next, the peripheral controller 48 and central controller 46 actuate the drive motor 136 to rotate 139 the arm 130 by 180° about its longitudinal axis 138 (FIG. 7D). This action flips the seeds over by placing the previously empty tray 26' (which is now full of flipped seeds) on the bottom of the stacked facing plates. The effect of this is to exchange the trays 26/26' for each other. The upper suction cup 132 (which was the lower of the two suction cups prior to the flip) is then actuated by the peripheral controller 48 and central controller 46 to hold tray 26 (which was the lower of the stacked facing trays prior to the flip). At or about the same time, the piston 140 is again raised to the actuated position such that it is in support of the bottom one of the stacked facing trays (compare to FIG. 7C). The peripheral controller 48 and central controller 46 then causes the upper suction cup 132 to hold the tray 26 and the gripper 134 to release its clamp on the two stacked facing trays, thus allowing the trays to be separated from each other. The translation stage 131 then withdraws the arm back to its retracted position (compare to FIG. 7B). The piston 140, which is supporting the lower, seed filled tray (now tray 26'), is then withdrawn by the peripheral controller 48 and central controller 46 back to the un-actuated location, and in so doing it returns the seed filled tray back into position in the cut-out 106 (compare to FIG. 7A).

A functionality for reaching out and grabbing a tray, like that provided by the arm 130, may also be useful in connection with the operation of the imaging subsystem 30. For example, in the situation where the camera 110 for the imaging subsystem 30 implements NMR/MRI imaging techniques, the gripping arm 130 can be used to remove the tray 26 from the transport subsystem 28 and insert the tray within the imager so that MRI data can be obtained. For example, the arm 130 could insert the tray within the bore of a conventional clinical or medical MRI instrument. Following completion of the MRI scan of the inserted tray (with its seeds), the arm 130 can function to retrieve and return the tray back to the transport subsystem 28. In this implementation, there would be no need for a flipping action since the MRI data will be acquired as image slices through the seeds.

Perspective views of a preferred implementation of the flip subsystem 42 are shown in FIGS. 9B and 9E. FIGS. 9B and 9E provide further detailed information concerning the flip subsystem 42 implementation. For example, a frame 17 is provided to support the various component parts of the flip subsystem 42 and facilitate its interconnection with other subsystems of the system 10.

While FIG. 7A-7D were schematic in nature, FIGS. 9B and 9E detail the preferred implementation for the arm 130 of the flip subsystem 42. FIG. 9F provides a perspective view of the arm 130 itself. It will be noted that the preferred implementation illustrates that the two stacked facing trays are gripped at their edges using a scissor-like linkage assembly 133 (as opposed to top/bottom gripping as schematically illustrated and described above). This type of gripping mechanism is preferred as it will not interfere with the placement and operation of the suction cups 132.

Figure 8:
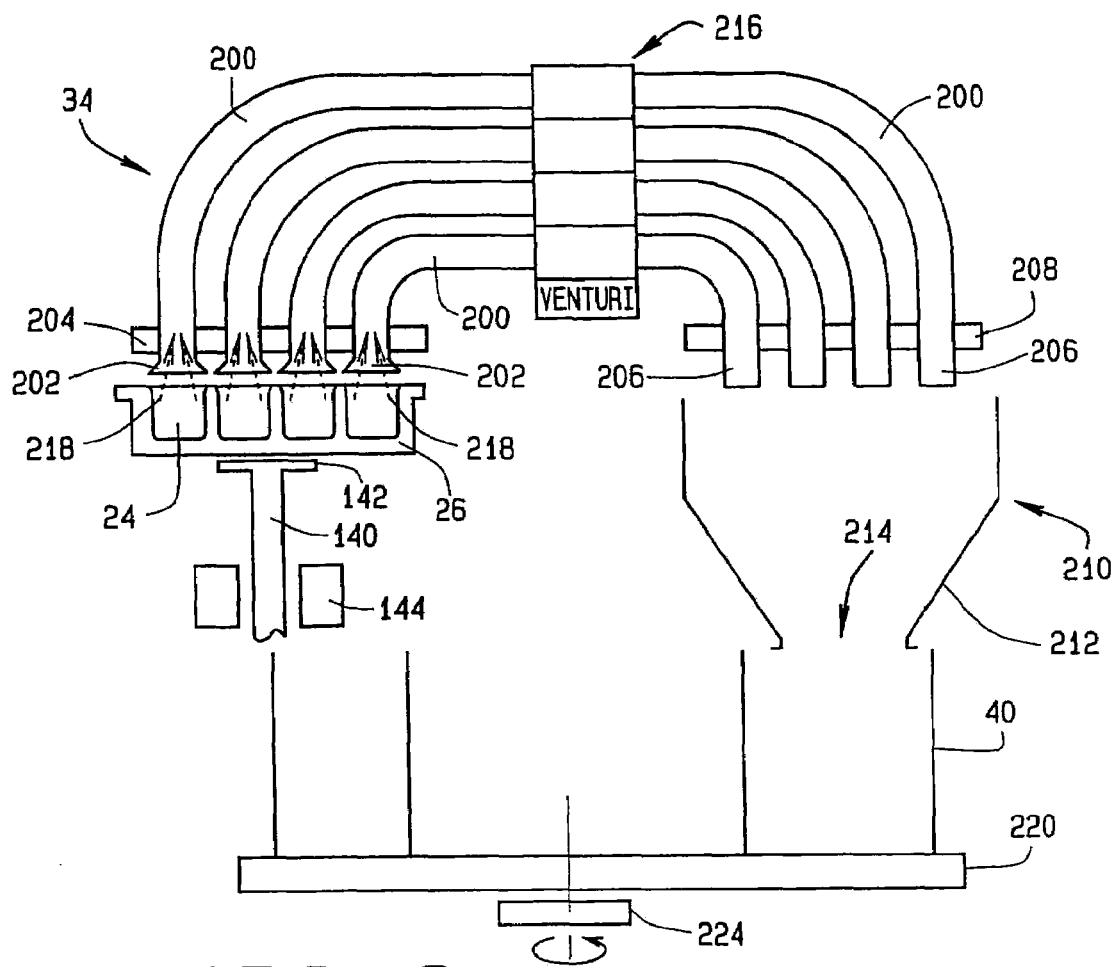
FIG. 8 is a schematic side view of one embodiment for the sorting subsystem utilized within the system of FIG. 1.

Reference is now made to FIG. 8 wherein there is shown a schematic side view of one embodiment for the sorting subsystem 34 utilized within the system of FIG. 1. The sorting subsystem 34 is comprised of an unloading portion which includes a plurality of selectively actuable suction tubes 200. Each of these tubes 200 has a first end 202 which is positioned by a bracket 204 to be located over a well 24 in a tray 26 that has been positioned underneath the sorting subsystem 34 by successive rotational advancement of the turntable support 102 of the transport subsystem 28. Thus, the plurality of tubes 200 at the ends 202 are arranged with a number and position to correspond with the number and position of the wells 24 in the tray 26. The tubes 200 further each have a second end 206 which is positioned by a bracket 208 over a collection pan 210 having downwardly sloped sides 212 which terminate at an opening 214. At about a midpoint of each tube is positioned a Venturi block 216 which may be selectively actuated by the peripheral controller 48 and central controller 46 to draw a suction 218 at the end 202 of the selected tube 200.

The sorting subsystem 34 is further comprised of a sorting portion which includes a rotatable turntable 220 that is positioned generally underneath the opening 214 in the collection pan 210. The top surface of the turntable 220 supports placement of a plurality of individual sort bins 40. More specifically, the rotatable turntable 220 is positioned beneath the collection pan 210 of the unloading portion such that individual ones of the sort bins 40 can be selectively located, through appropriate rotation of the turntable 220 directly under the opening 214. Movement of the turntable 220 is effectuated through the use of a motor 224 (preferably a stepper-type motor). Actuation of the turntable 220 to rotate a selected one of the sort bins 40 into proper position below the opening 214 is controlled by the peripheral controller 48 and central controller 46.

The sorting subsystem 34 is further comprised of a lifting portion which includes a linear air piston 140 which is generally located in alignment with the location of the unloading portion described above. More specifically, the piston 140 is located such that it is aligned with a center of the area of the sector 104 of the turntable support 102 where the cut-outs 106 holding seed filled trays 26 are located with each successive rotational advancement. When positioned in an un-actuated position (compare to FIG. 7A), end 142 of the piston 140 is located such that it is below the transport subsystem 28. More specifically, the end 142 would be below the turntable support 120 and any tray 26 held thereby. An air drive 144 operates under the control of the peripheral controller 48 and central controller 46 (see, FIG. 1) to linearly move the piston 140 between its un-actuated position and an actuated position (compare to FIG. 7B and see FIG. 8). When moving towards the actuated position, the end 142 of the piston 140 passes through the cut-out 106 in the turntable support 102 to raise a tray 26 above the top surface of the transport subsystem 28. When the piston 140 returns to the un-actuated location, a tray 26 is lowered back into position in the cut-out 106.

In operation, the peripheral controller 48 and central controller 46 make a determination as to the sort bin 40 to which each seed 16 (held within a well 24 of a tray 26) is to be delivered by the sorting subsystem 34. In a preferred embodiment, this sorting determination is made by the central controller 46 based on its analysis of the seed image data collected by the imaging subsystem 30 (as discussed above by linking seed characteristics to individual seeds). Thus, an identification is made based on the imaging data (for example, seed characteristics) of which seeds (in wells 24) are to be sorted into which of the sort bins 40. Other sorting determinations as selected by the user could alternatively be implemented.

Following transport of the tray 26 by the transport subsystem 28 into position under the plurality of tubes 200, the peripheral controller 48 and central controller 46 actuates the turntable 220 to move a selected one of the sort bins 40 into position under the opening 214, and further actuates the lifting portion of the sorting subsystem 34 to raise the tray 26 into position directly underneath the ends 202 of the tubes 200. The peripheral controller 48 and central controller 46, with knowledge of the particular wells 24 containing seeds identified in the sorting determination to be deposited into the selected and positioned sort bin 40, then selectively actuates one or more of the Venturi blocks 216 for the tubes 200 whose ends 202 are positioned over those particular wells 24 in the tray 26 (containing seeds to be sorted into the selected sort bin 40). Actuation of the Venturi block(s) 216 causes a suction to be drawn at the end 202 of the tube 200 which draws the seed(s) 16 contained in the corresponding well(s) 24 into the tube(s) 200. Under the Venturi/suction forces, the captured seed is conveyed by an air stream through the tube 200 to the end 206 where it is deposited into the collection pan 210. Once in the pan 210, gravity acts on the seed causing it to fall through the opening 214 and into the positioned sort bin 40. The process then repeats by selectively moving another sort bin 40 into position and selectively actuating the Venturi block(s) 216 to suck selected seeds from the wells 24 for deposit into the selected bin. When the tray 26 has been cleared of seeds, the peripheral controller 48 and central controller 46 de-actuates the lifting portion of the sorting subsystem 34 to lower the empty tray 26 back into position in the cut-out 106 of the turntable.

It will be understood that the sorting subsystem 34 preferably includes the same number of tubes 200 (having the same arrangement) as the divided tray 26 has well locations 24. For example, if the divided tray has 24 well locations in a 4×6 array format, then the sorting subsystem 34 should correspondingly have 24 tubes 200 also in a 4×6 array format. In this way, one divided tray 26 of seeds can be fully unloaded using actuation of the sorting subsystem 34 under the control of the peripheral controller 48 and central controller 46 without having to engage in any positional adjustment of the subsystems. An even submultiple arrangement with an appropriate x-y translation stage (such as discussed earlier for loading) could alternatively be used for unloading and sorting.

Figure 9G:
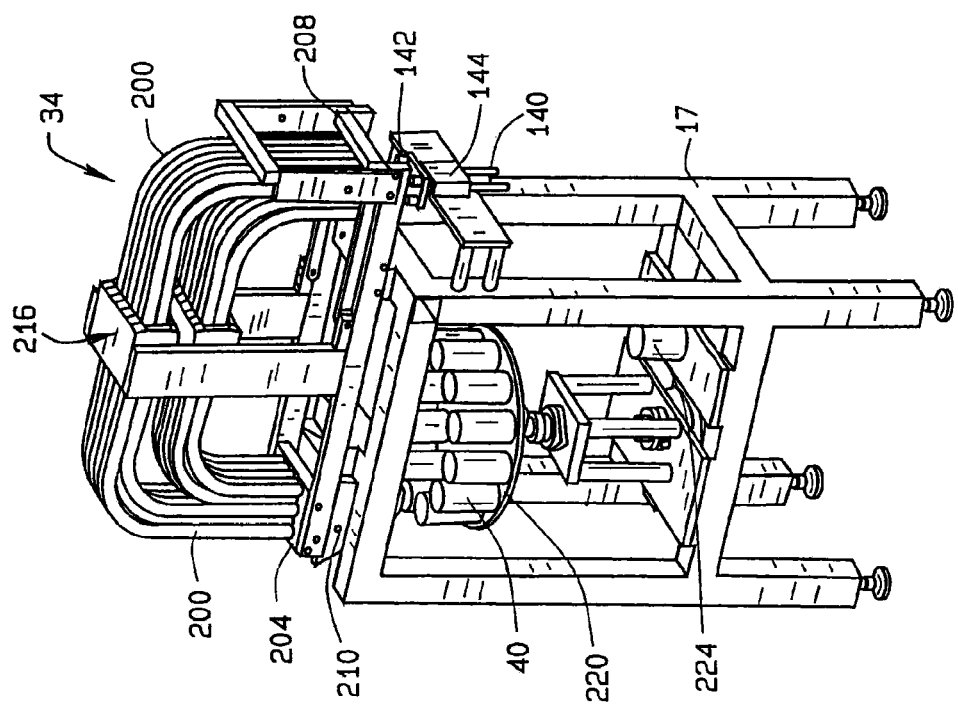
FIG. 9G is a perspective view of the sorting subsystem.

Perspective views of a preferred implementation of the sorting subsystem 34 are shown in FIGS. 9B and 9G. FIGS. 9B and 9G provide further detailed information concerning the sorting subsystem 34 implementation. For example, a frame 17 is provided to support the various component parts of the sorting subsystem 34 and facilitate its interconnection with other subsystems of the system 10.

Reference is now made to FIG. 9A wherein there is shown a top view of the seed handling system 10 utilizing the subsystems disclosed herein. For ease of illustration, the turntable support 102 is shown with only four sectors 104. It will, of course, be understood that as many sectors 104 as are needed (odd or even) could be accommodated with an appropriately sized design. FIG. 9A illustrates one of many possible arrangements of the subsystems for the seed handling 10 of the present invention. For ease of reference, clock positions are used to describe subsystem locations (stations). The loading subsystem 18 is positioned at nine-o'clock, the imaging subsystem 30 and flip subsystem 42 are positioned at twelve-o'clock, and the sorting subsystem 34 is positioned at three-o'clock.

The system 10 operates as follows. An empty tray 26 advances by one sector from the six-o'clock position to the nine-o'clock position by rotating the turntable support 102. When the opening 106/tray 26 is positioned in alignment with the loading subsystem 18 station, individual ones 14 of the seeds 16 are picked and deposited on the tray, one seed per well 14 (see, FIGS. 2A-2B and 3A-3B). Following completion of the loading operation, the seed filled tray 16 is conveyed by the transport subsystem 28 to the twelve-o'clock area of the imaging subsystem 30 (and flip subsystem 42, if needed) by advancing the rotation of the turntable support by one sector until the opening 106/tray 26 is positioned in proper alignment at the station for imaging (and flipping, if desired). The imaging subsystem 30 (shown in dotted lines so as to not obscure operations at the twelve-o'clock position) then acquires an image of (a first side of) each of the seeds contained within the wells 24. In the event it is desirable to obtain multi-side images of the seeds, the flip subsystem 42 is then activated (see, FIGS. 7A-7D) to flip the seeds over. The imaging subsystem 30 then acquires an image of (a second side of) each of the seeds contained within the wells 24. It will be recognized that the seeds occupy mirror image positions in the two images obtained by the imaging subsystem 30 and this factor is accounted for by either the imaging subsystem or the central controller in connection with associating multiple images with a single seed for further processing. Following completion of the imaging/flipping operation, the seed filled tray 26 is conveyed by the transport subsystem 28 to the three-o'clock area of the sorting subsystem 34 by advancing the rotation of the turntable support by one sector until the opening 106/tray 26 is positioned in proper alignment with the tubes of the sorting subsystem station. While this positional advancement is made, the central controller processes the image data collected by the imaging subsystem in order to make certain analyses and evaluations which drive the sort determination. For example, the image data for each seed in the tray is processed to determine whether each seed possesses certain characteristics of interest (such as, trait, damage, disease, color, size, and the like). By the time the positional advancement to the sorting subsystem 34 is completed, the central controller has made a sorting determination as to where (i.e., into which sort bin 40 including, perhaps, rejection) each seed must be deposited. The sorting subsystem 34 then operates the turntable 220 to move the proper one or ones of the sort bins 40 into position and the actuates the proper one or ones of the Venturi blocks 216 to draw the seed(s) from the well(s) for delivery to the positioned bin (see, FIG. 8). This operation is repeated as many times as is needed to remove all seeds from the tray. The empty tray 26 is then conveyed by the transport subsystem 28 to the six-o'clock area station by advancing the rotation of the turntable support by one sector, and the process with respect to that tray is repeated.

Although the operation of the system 10 with respect to a single tray 26 has been described, it will be understood that multiple trays are handled simultaneously by the system thus further increasing its throughput. For example, in the system 10 illustrated in FIG. 9A, four trays 26 are capable of simultaneous handling. In such an operation, the subsystems are simultaneously active in performing their assigned task(s) with each rotational advancement of the turntable support 102. Thus, while one tray of seeds is being loaded by the loading subsystem 18, previously loaded trays of seeds are being processed at the imaging subsystem 30 and sorting subsystem 34.

Figure 10:
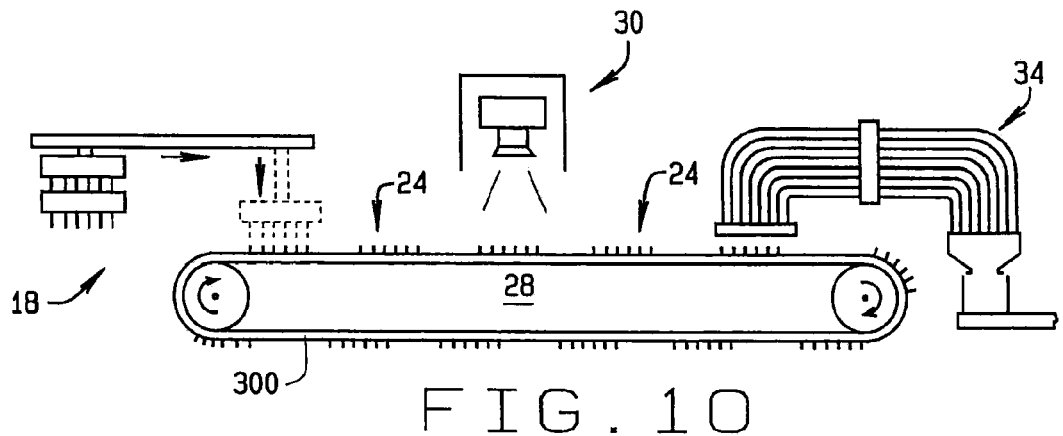
FIG. 10 is an alternative embodiment of the system of the present invention.

Reference is now made to FIG. 10 wherein there is shown an alternative embodiment of the system of the present invention. In this embodiment, the transport subsystem 28 is an endless belt 300. Molded into an outer surface of the belt 300 are a plurality of wells 24 arranged in consecutive rows. The spacing between consecutive rows may be selected by the user. Additionally, for certain applications, a plurality of consecutive rows may be grouped together to form an n x m matrix of wells similar to a tray 26 (as shown). The belt 300 is driven by a motor (preferably a stepper motor) which can be controlled to cause the belt to advance a selected amount in much the same way the turntable 100 rotation advancement is controlled as discussed above. In this way, like with the previous embodiment, a certain number of wells (or group of wells) are accurately advanced forward from station to station.

Like with the turntable-based implementation, a loading subsystem 18, imaging subsystem 30 and sorting subsystem 34 are positioned at separate stations along the conveyance path. This belt implementation with integrated wells 24 cannot perform seed flipping in the same manner as that provided with the turntable implementation.

Operation of the belt-based system is analogous to that of the turntable-based system as described in connection with FIG. 9A. Empty row(s) of wells 24 are advanced by the belt motor into position underneath the loading subsystem 18. The loading subsystem 18 operates in the same manner discussed above and shown in FIGS. 2A-2B and 3A-3B to load individual wells 24 with seeds. The belt motor then advances those seed-filled wells into position underneath the imaging subsystem 30. For an NMR/MRI imaging implementation, the belt may be configured to pass through the bore of the MRI instrument. The imaging subsystem 30 operates in the same manner discussed above and shown in FIG. 6 to obtain seed images. The belt motor then advances the seed filled wells further into position underneath the sorting subsystem 34. The sorting subsystem 34 operates in the same manner as discussed above and shown in FIG. 8 to selectively remove seeds from the wells and deliver them to certain sort bins 40. Following removal of the seeds, the belt motor advances the empty wells back around and the cycle repeats.

Figure 11:
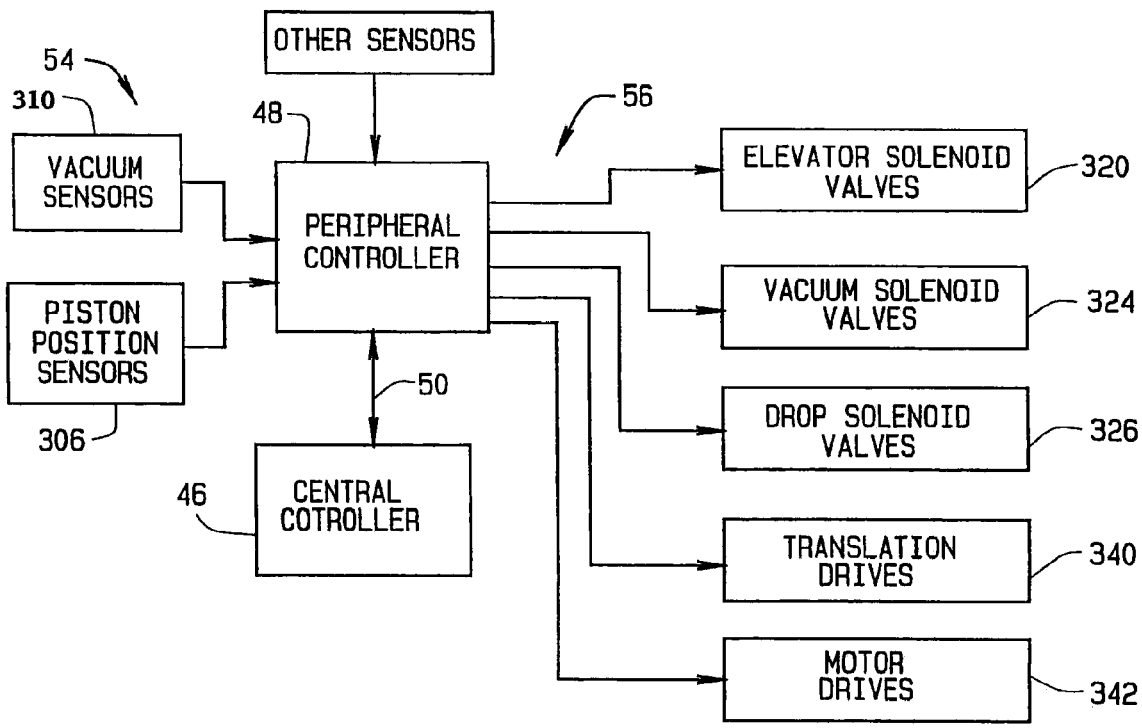
FIG. 11 is a schematic diagram of the control operation for the system of the present invention.

Reference is now made to FIG. 11 wherein there is shown a schematic diagram of the control operation for the system 10 of the present invention. The peripheral controller 48 is directly in charge of managing system operation. The peripheral controller 48 operates under the control and direction of the central controller 46 (see, FIG. 1). Taking the configuration of the system 10 shown in FIG. 1 as an example, the peripheral controller 48 receives a number of sensor 54 inputs.

Vacuum sensors 310 are used in connection with the FIGS. 2A-2B loading subsystem 18 to sense, based on vacuum pressure, when seeds have been successfully held by the plurality of vacuum cups 90. One such sensor is needed for each vacuum cup 90. Similarly, the sensors 300 are used in connection with the FIGS. 7A-7D flip subsystem 42 to sense, based on vacuum pressure, when a tray 26 has been successfully held by the vacuum cup 132.

Piston position sensors (for up and down) 306 are used in connection with the FIG. 2A-2B loading subsystem 18 operation to sense the position of the pistons 66 and assist in making piston actuation start and stop decisions. Similar piston position sensors 306 are needed in connection with the FIGS. 7A-7D flip subsystem 42 operation to sense the position of the pistons 66 and assist in making piston actuation start and stop decisions.

The peripheral controller 48 further exercises control (generally illustrated by arrow 56 in FIG. 1) over the operations and actions taken by the various components of the system 10. Taking the configuration of the system 10 shown in FIG. 1 as an example, the peripheral controller 48 controls elevator solenoid valves 320 to pneumatically actuate the piston 66 and the piston 140 (through the air drives 72 and 144) to move between the up and down positions (as sensed by the sensors 306) as shown in FIGS. 2A-2B and 7A-7D. Vacuum solenoid valves 324 are controlled by the peripheral controller 48 to cause a vacuum to be drawn at the vacuum cups 90 that hold the picked seeds within the selection subsystem 18 (FIGS. 2A-2B) and the vacuum cup 132 that holds the tray 26 within the flip subsystem 42 (FIGS. 7A-7D). These valves 324 are further used to cause a suction to be drawn at the ends 202 of the tubes 200 within the sorting subsystem 34 to extract seeds from well locations in the tray 26 during off-loading (FIG. 8). More specifically, each of these valves 324 allow pressurized air to be input to a Venturi block (like the block 216) that is used for the purpose of drawing a suction. In connection with the operation of the vacuum cups 90, the peripheral controller 48 may further control drop solenoid valves 326 which allow pressurized air to be applied to the vacuum cups to blow a held seed away. This may be useful to assist gravitational forces in dropping the held seeds from the vacuum cups 90. Preferably, the valves 326 are actuated when the valves 324 are un-actuated (and vice-versa).

The peripheral controller 48 still further actuates a driver 340 to control operation of the translation stage 94 in the loading subsystem 18 so that the vacuum cups 90 can be accurately positioned over both the pistons 66 and the wells 24. Similarly, the driver 340 is actuated by the peripheral controller 48 to control the translation stage 131 so as to move the arm 130 in the flip subsystem 42 between its extended and retracted positions and also cause flipping rotation.

The peripheral controller 48 also actuates a driver 342 to control operation of the stepper motor for the turntable 100 (in the transport subsystem 28) such that the turntable is only advanced the appropriate rotational amount to move the trays 26 between stations. Similarly, the driver 342 is actuated by the peripheral controller 48 to control the turntable 220 (in the sorting subsystem 34) such that the turntable is only advanced the appropriate rotational amount to move the sort bins 40 underneath the opening 214.

Although preferred embodiments of the method and apparatus of the present invention have been illustrated in the accompanying Drawings and described in the foregoing Detailed Description, it will be understood that the invention is not limited to the embodiments disclosed, but is capable of numerous rearrangements, modifications and substitutions without departing from the spirit of the invention as set forth and defined by the following claims.

What is claimed is:

1. A system for processing biological samples, the system comprising:
   at least two or more divided trays each comprising a plurality of sample wells;
   a transport subsystem operable to convey each of the at least two or more divided trays between each of a plurality of stations;
   a loading subsystem positioned at a first station and operable to load a biological sample into a well of at least one of the at least two or more divided trays;
   an imaging subsystem positioned at a second station and operable to image the biological sample to obtain sample image data; and
   a sorting subsystem positioned at a third station and operable to sort the biological sample into a selected one of a plurality of sort bins.

2. The system as set forth in claim 1 wherein the transport subsystem comprises a turntable supporting the at least two or more divided trays and which is selectively rotated to advance the at least two or more divided trays in a loop from the first station to the second station to the third station and back to the first station.

3. The system as set forth in claim 1 wherein the transport subsystem comprises an endless belt supporting the at least two or more divided trays and which is selectively rotated to advance the at least two or more divided trays in a loop from the first station to the second station to the third station and back to the first station.

4. The system as set forth in claim 1 wherein the sorting subsystem operates to sort the biological sample based on the sample image data.

5. The system as set forth in claim 1 wherein the imaging subsystem includes a visible light camera to image the biological sample.

6. The system as set forth in claim 1 wherein the imaging subsystem includes an infra-red light camera to image the biological sample.

7. The system as set forth in claim 1 wherein the imaging subsystem includes an MRI instrument to image the biological sample.

8. The system as set forth in claim 1 further including a flip subsystem operable to flip the biological sample.

9. The system as set forth in claim 8 wherein the flip subsystem and imaging subsystem operate in a coordinated manner to allow the imaging subsystem to obtain a first image of the biological sample prior to being flipped and a second image of the biological sample after being flipped.

10. The system as set forth in claim 1 wherein the biological sample comprises an agricultural seed.

11. A method, comprising:
    conveying at least two or more divided trays each comprising a plurality of sample wells between each of a plurality of stations;
    at a first station, loading a biological sample into a well of one of the at least two or more divided trays;
    at a second station, imaging the biological sample to obtain sample image data; and
    at a third station, sorting the biological sample into a selected one of a plurality of sort bins.

12. The method of claim 11 wherein the step of conveying comprises selectively advancing the at least two or more divided trays in a loop from the first station to the second station to the third station and back to the first station.

13. The method of claim 11 wherein the step of sorting comprises sorting the biological sample based on the sample image data.

14. The method of claim 11 wherein the step of imaging comprises obtaining at least one or more visible light images of the biological sample.

15. The method of claim 11 wherein the step of imaging comprises obtaining at least one or more infra-red light images of the biological sample.

16. The method of claim 11 wherein the step of imaging comprises obtaining at least one or more MRI images of the biological sample.

17. The method of claim 11 further including the step of flipping the biological sample.

18. The method of claim 17 wherein the step of flipping and the step of imaging are performed in a coordinated manner to allow the step of imaging to obtain a first image of the biological sample prior to being flipped and a second image of the biological sample after being flipped.

19. The method of claim 11 wherein the biological sample comprises an agricultural seed.

20. The method of claim 11 further including the step of processing the sample image data to obtain characteristic information concerning the biological sample, the step of sorting further including the step of sorting the biological sample based on the obtained characteristic information.

21. The method of claim 20 wherein the characteristic information comprises one of size and shape of the biological sample.

22. The method of claim 20 wherein the characteristic information comprises one of damage or disease in the biological sample.

23. The method of claim 20 wherein the characteristic information comprises biochemical information for the biological sample.

24. The method of claim 23 wherein the biochemical information comprises biochemical trait information.

25. A high throughput system for processing a plurality of biological samples, the system comprising:
    at least two or more divided trays each comprising a plurality of sample wells;
    a loading subsystem positioned at a first station and operable to load a biological sample into a sample well of one of the at least two or more divided trays while said one of the at least two or more divided trays is located at the first station;
    an imaging subsystem positioned at a second station and operable to image the biological sample within the sample well of said one of the at least two or more divided trays to obtain sample image data while said one of the at least two or more divided trays is located at the second station;
    a sorting subsystem positioned at a third station and operable to remove the biological sample from a sample well and sort the biological sample into a selected one of a plurality of sort bins while one of the at least two or more divided trays is located at the third station; and
    a transport subsystem operable to convey the at least two or more divided trays between the first, second, and third stations such that the plurality of sample wells of each of the at least two or more divided trays are together disposed at the same station for each operation of each station.

26. The system as set forth in claim 25 wherein the transport subsystem comprises a turntable supporting the at least two or more divided trays and which is selectively rotated to advance the at least two or more divided trays in a loop from the first station to the second station to the third station and back to the first station.

27. The system as set forth in claim 25 wherein the biological sample comprises an agricultural seed.

28. The system as set forth in claim 25 wherein the transport subsystem comprises an endless belt supporting the at least two or more divided trays and which is selectively rotated to advance the at least two or more divided trays in a loop from the first station to the second station to the third station and back to the first station.

29. The system as set forth in claim 25 further comprising a flip subsystem operable to flip the biological sample.

30. The system as set forth in claim 29 wherein the flip subsystem and imaging subsystem operate in a coordinated manner to allow the imaging subsystem to obtain a first image of the biological sample prior to being flipped and a second image of the biological sample after being flipped.

31. The system as set forth in claim 25 wherein the sorting subsystem operates to sort the biological sample based on the sample image data.

32. The system as set forth in claim 25 wherein the imaging subsystem includes a visible light camera to image the biological sample.

33. The system as set forth in claim 25 wherein the imaging subsystem includes an infra-red light camera to image the biological sample.

34. The system as set forth in claim 25 wherein the imaging subsystem includes an MRI instrument to image the biological sample.

* * * * *

UNITED STATES PATENT AND TRADEMARK OFFICE
CERTIFICATE OF CORRECTION

PATENT NO.       : 7,600,642 B2                                        Page 1 of 1
APPLICATION NO.  : 10/945811
DATED            : September 21, 2004
INVENTOR(S)      : Kevin L. Deppermann It is certified that error appears in the above-identified patent and that said Letters Patent is hereby corrected as shown below:

COVER PAGE
On the cover page, the following Related U.S. Application Data should be added:

Related U.S. Application Data

(60)   Provisional application No. 60/505,270, filed September 23, 2003.

SPECIFICATION (CROSS REFERENCE TO RELATED APPLICATIONS)
Column 1, line 7: before "The present application is related to" add "This application claims priority from U.S. Provisional Patent Application Serial No. 60/505,270 (filed September 23, 2003), the entire disclosure of which is incorporated herein by reference."

Signed and Sealed this

First Day of December, 2009

David J. Kappos
*Director of the United States Patent and Trademark Office*